US007404799B1

(12) United States Patent
Koh

(10) Patent No.: US 7,404,799 B1
(45) Date of Patent: Jul. 29, 2008

(54) SYSTEM AND METHOD FOR DETECTION OF RESPIRATION PATTERNS VIA INTEGRATION OF INTRACARDIAC ELECTROGRAM SIGNALS

(75) Inventor: Steve Koh, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 415 days.

(21) Appl. No.: 11/100,189

(22) Filed: Apr. 5, 2005

(51) Int. Cl.
A61B 5/02 (2006.01)
A61B 5/04 (2006.01)
A61B 5/08 (2006.01)
A61N 1/00 (2006.01)

(52) U.S. Cl. .......... 600/484; 600/513; 600/529; 600/509; 600/483; 607/9; 607/20; 607/17; 607/18; 607/19

(58) Field of Classification Search .......... 600/481, 600/483, 484, 500–504, 508–526, 529, 536, 600/547; 607/1–38
See application file for complete search history.

(56) References Cited

U.S. PATENT DOCUMENTS

| | | | |
|---|---|---|---|
| 4,089,959 A | 5/1978 | Diamond | 424/253 |
| 4,757,815 A | 7/1988 | Strandberg et al. | 128/419 PG |
| 5,003,976 A * | 4/1991 | Alt | 607/18 |
| 5,056,519 A | 10/1991 | Vince | 128/419 G |
| 5,476,483 A | 12/1995 | Bornzin et al. | 607/17 |
| 5,911,218 A | 6/1999 | DiMarco | 128/200.24 |
| 6,128,534 A | 10/2000 | Park et al. | 607/17 |
| 6,331,536 B1 | 12/2001 | Radulovacki et al. | 514/214.02 |
| 6,415,183 B1 | 7/2002 | Scheiner et al. | 607/42 |
| 6,432,956 B1 | 8/2002 | Dement et al. | 514/252.1 |
| 6,449,509 B1 | 9/2002 | Park et al. | 607/20 |
| 6,512,952 B2 | 1/2003 | Stahmann et al. | 607/9 |
| 6,519,493 B1 | 2/2003 | Florio et al. | 607/9 |
| 6,525,073 B2 | 2/2003 | Mendel et al. | 514/337 |
| 6,586,478 B2 | 7/2003 | Ackman et al. | 514/738 |
| 6,628,988 B2 | 9/2003 | Kramer et al. | 607/9 |
| 6,643,546 B2 | 11/2003 | Mathis et al. | 607/9 |
| 6,697,672 B2 | 2/2004 | Andersson | 607/17 |
| 6,830,548 B2 | 12/2004 | Bonnet et al. | 600/529 |
| 6,904,320 B2 * | 6/2005 | Park et al. | 607/17 |
| 7,025,729 B2 * | 4/2006 | de Chazal et al. | 600/508 |
| 7,225,021 B1 * | 5/2007 | Park et al. | 607/18 |
| 7,324,845 B2 * | 1/2008 | Mietus et al. | 600/513 |
| 7,343,199 B2 * | 3/2008 | Hatlestad et al. | 600/513 |
| 2002/0095189 A1 | 7/2002 | Andersson | 607/25 |
| 2003/0216789 A1 | 11/2003 | Deem et al. | 607/9 |
| 2004/0134496 A1 * | 7/2004 | Cho et al. | 128/204.23 |
| 2005/0085865 A1 * | 4/2005 | Tehrani | 607/42 |
| 2005/0085866 A1 * | 4/2005 | Tehrani | 607/42 |
| 2005/0113710 A1 * | 5/2005 | Stahmann et al. | 600/534 |
| 2005/0137487 A1 * | 6/2005 | Zhu et al. | 600/513 |
| 2005/0197588 A1 * | 9/2005 | Freeberg | 600/529 |
| 2005/0256418 A1 * | 11/2005 | Mietus et al. | 600/512 |

FOREIGN PATENT DOCUMENTS

EP 1 192 971 B1 4/2002

* cited by examiner

*Primary Examiner*—Navin Natnithithadha

(57) ABSTRACT

Techniques are provided for tracking patient respiration based upon intracardiac electrogram signals or other electrical cardiac signals. Briefly, respiration patterns are detected by integrating cardiac electrical signals corresponding to individual paced cardiac cycles. The integrals may be obtained between consecutive pairs of ventricular pacing pulses or between consecutive pairs of atrial pacing pulses. In either case, cyclical changes in the integrals of the individual cardiac cycles are tracked. The cyclical changes are representative of respiration. Once respiration patterns have been identified, episodes of abnormal respiration, such as apnea, hyperpnea, nocturnal asthma, or the like, may be detected and therapy automatically delivered.

20 Claims, 10 Drawing Sheets

SYSTEM AND METHOD FOR DETECTION OF RESPIRATION PATTERNS VIA INTEGRATION OF INTRACARDIAC ELECTROGRAM SIGNALS

FIELD OF THE INVENTION

The invention generally relates to implantable medical devices, such as pacemakers or implantable cardioverter/defibrillators (ICDs), and in particular, to techniques for detecting respiration patterns within a patient in which a medical device is implanted, including abnormal respiration patterns such as apnea, hypopnea or nocturnal asthma.

BACKGROUND OF THE INVENTION

It is highly desirable to reliably track respiration within patients having pacemakers and ICDs. Tracking patient respiration permits potentially dangerous respiratory disorders, such as apnea, hypopnea, hyperpnea, nocturnal asthma, and Cheyne-Stokes Respiration (CSR), to be detected. Apnea and hypopnea are abnormal respiration patterns characterized by periods of significantly reduced respiration. With hypopnea, respiration is reduced but still present. With apnea, however, respiration may cease completely for 10 seconds or longer. One common form of apnea is sleep apnea, in which hundreds of individual episodes of apnea can occur during a single night. Accordingly, patients with sleep apnea experience frequent wakefulness at night and excessive sleepiness during the day. In addition, apnea can exacerbate various medical conditions, particularly congestive heart failure (CHF) wherein the patient suffers from poor cardiac function. Indeed, the aberrant blood chemistry levels occurring during sleep apnea are a significant problem for patients with CHF. Due to poor cardiac function caused by CHF, patients already suffer from generally low blood oxygen levels. Frequent periods of sleep apnea result in even lower blood oxygen levels.

Episodes of apnea can also occur during Cheyne-Stokes Respiration (CSR), which is an abnormal respiratory pattern often occurring in patients with CHF. CSR is characterized by alternating periods of hypopnea and hyperpnea (i.e. fast, deep breathing.) Briefly, CSR arises principally due to a time lag between blood $CO_2$ levels sensed by the respiratory control nerve centers of the brain and the blood $CO_2$ levels. With CHF, poor cardiac function results in poor blood flow to the brain such that respiratory control nerve centers respond to blood $CO_2$ levels that are no longer properly representative of the overall blood $CO_2$ levels in the body. Hence, the respiratory control nerve centers trigger an increase in the depth and frequency of breathing in an attempt to compensate for perceived high blood $CO_2$ levels—although the blood $CO_2$ levels have already dropped. By the time the respiratory control nerve centers detect the drop in blood $CO_2$ levels and act to slow respiration, the blood $CO_2$ levels have already increased. This cycle becomes increasingly unbalanced until respiration alternates between hypopnea and hyperpnea. The periods of hypopnea often become sufficiently severe that no breathing occurs between the periods of hyperpnea, i.e. periods of frank apnea occur between the periods of hyperpnea. The wildly fluctuating blood chemistry levels caused by alternating between hyperpnea and apnea/hypopnea can significantly exacerbate CHF and other medical conditions. When CHF is still mild, CSR usually occurs, if at all, only while the patient is sleeping. When it becomes more severe, CSR can occur while the patient is awake.

Abnormal respiration during sleep may also arise due to nocturnal asthma. With asthma, the linings of the airways swell and become more inflamed. Mucus clogs the airways and the muscles around the airways tighten and narrow. Hence, breathing becomes difficult and stressful. During an asthma attack, rapid breathing patterns similar to hyperpnea occur, though little or no oxygen actual reaches the lungs. An asthma attack may be triggered by allergens, respiratory infections, cold and dry air, or even heartburn. The majority of asthma attacks occur during the night, between 3:00 a.m. and 5:00 a.m. Nocturnal asthma has been associated with factors such as decreased pulmonary function, hypoxemia and circadian variations of histamine, epinephrine, and cortisol concentrations. Asthma attacks at night may also be triggered directly by sleep apnea. Nocturnal asthma attacks may be fatal, particularly within patients also suffering from CHF.

In view of the significant adverse consequences of apnea/hypopnea, nocturnal asthma, or CSR, particularly insofar as patients with CHF are concerned, it is highly desirable to provide techniques for detecting such conditions. Tracking actual patient respiration provides perhaps the most direct and effective technique for detecting respiratory disorders. For patients with pacemakers and ICDs, respiration is conventionally tracked based on thoracic impedance as measured via pacing/sensing leads implanted within the heart. Sensing of the intracardiac electrogram (IEGM) of the patient is temporarily suspended during each cardiac cycle so as to sense an impedance signal, from which respiration patterns are derived. See, for example, U.S. Pat. No. 6,449,509 to Park et al., entitled "Implantable Stimulation Device Having Synchronous Sampling for a Respiration Sensor."

Although impedance-based techniques are useful, it would be desirable to provide alternative techniques for tracking respiration, particularly for the purposes of detecting episodes of abnormal respiration, wherein respiration is derived solely from the IEGM signal so as to eliminate the need to detect or process impedance. Additionally, this eliminates need for additional sensors, and the sensing electrodes can be thus used for IEGM based breathing pattern detection and hence, the ease of implementability in current platforms. One technique for deriving respiration from an IEGM signal is set forth in U.S. Pat. No. 6,697,672 to Andersson, entitled "Implantable Heart Stimulator." Briefly, Andersson provides a technique to extract parameters related to patient respiration from an analysis of intervals between various events detected within a ventricular-IEGM (i.e. V-IEGM) signal. For example, cycle-to-cycle variability is tracked in R-R intervals or in the amplitude of S-T intervals. In other words, the technique of Andersson exploits changes in the durations of intervals within the V-IEGM to track respiration. Although not discussed in the Andersson reference, it is believed that autonomic variability arising during respiration causes the changes in intervals. R-waves (also referred to as QRS-complexes) are electrical signals representative of the depolarization of ventricular muscle tissue. The subsequent electrical repolarization of the ventricular tissue appears within the IEGM as a T-wave. Electrical depolarization of atrial muscle tissue is manifest as a P-wave. Strictly speaking, P-waves, R-waves and T-waves are features of a surface electrocardiogram (EKG or ECG). For convenience, the terms P-wave, R-wave and T-wave are also used herein (and in the literature) to refer to the corresponding internal signal component.

Another technique is set forth in U.S. Patent Application 60/631,111, of Bharmi et al., entitled "System and Method for Detection of Respiration Patterns via Intracardiac Electrogram Signals," the disclosure of which is incorporated herein by reference. With the technique Bharmi et al., respiration patterns are detected based upon cycle-to-cycle changes in morphological features associated with individual electrical events with the IEGM signals. In one example, IEGM signals are sensed and individual cardiac cycles are identified therein. Selected individual electrical events (such as P-waves, QRS-complexes or T-waves) are identified within the cardiac cycles and one or more parameters associated with the individual features are detected (such as maximum amplitude, peak-to-peak amplitude, or numerical integral). Then, patient respiration is tracked based on cycle-to-cycle changes in the detected parameters associated with the individual selected electrical events. Hence, in contrast to the technique of Andersson, which primarily relates to changes in the duration of intervals, the technique of Bharmi et al. instead examines changes within the shape of individual features of the IEGM such as P-waves, QRS-complexes or T-waves. It is believed that that slight displacement of IEGM sensing electrodes caused by movement of the thorax during respiration causes slight variations in the size and shape of individual electrical events of the IEGM signals, such as P-waves, and that those changes are correlated with respiration. This differs from changes in the durations of intervals (such as R-R intervals), which, as noted, appear to arise due to autonomic variability.

Although the interval-based variability technique of Andersson and the individual feature-based technique of Bharmi et al. are both effective, it would be desirable to provide additional or alternative IEGM-based techniques for tracking respiration and it is to that end that the present invention is primarily directed. It is also desirable to provide techniques of detecting episodes of abnormal respiration from IEGM signals and other aspects of the invention are directed to that end as well.

SUMMARY

In accordance with one illustrative embodiment, techniques are provided for tracking respiration within a patient via an analysis of the integrals of electrical cardiac cycles (i.e. heart beats). In one example, pacing pulses are delivered to the heart and resulting cardiac electrical signals are sensed. Individual complete cardiac cycles are identified therein based, for example, on consecutive pairs of ventricular pacing pulses or consecutive pairs of atrial pacing pulses. Values representative of the integrals of the cardiac signals corresponding to individual complete cardiac cycles are then determined and patient respiration is then detected based on the values. In one specific example, the values representative of integrals are derived by calculating a numerical sum of the absolute values of a plurality of individual voltage samples of the cardiac signals within the complete cardiac cycle.

Preferably, the resulting respiration pattern is then analyzed to detect abnormal forms of respiration such as apnea, hypopnea, nocturnal asthma, or CSA. The technique can also be used to track and trend sleep disorder breathing or, in general, disordered breathing. Depending upon the capabilities of the implanted device, appropriate therapy is then delivered. For example, an alarm device may be triggered to alert the patient upon detection of an episode of apnea/hypopnea. The alarm device may be, e.g., an implanted device such as a "tickle" voltage warning device or a bedside warning system that emits an audible alarm. In this manner, if the patient is asleep, the patient is thereby awakened so as to prevent extended episodes of abnormal respiration from occurring, which can cause significant variances in blood chemistry that can exacerbate other medical conditions such as CHF.

In addition, if a determination has been made by the implanted system that the patient is subject to frequent episodes of apnea or hypopnea, dynamic atrial overdrive (DAO) pacing may be delivered in an effort to prevent additional episodes from occurring. If an implantable drug pump is provided, the implanted system may be programmed to selectively deliver medications deemed effective in addressing abnormal respiration or effective in addressing the underlying medical condition causing the abnormal respiration (which may be, e.g., CHF). In addition, regardless of the type of therapy, diagnostic information is preferably recorded within a memory of the implanted system for subsequent review by a physician.

Thus, by deriving respiration from IEGM signals, abnormal respiration can be detected using a pacemaker or ICD without requiring additional leads or sensors beyond those otherwise employed in cardiac sensing/pacing. In the alternative, the detection techniques of the invention may be implemented within other implantable devices besides pacemakers or ICDs, such as dedicated devices provided specifically for detecting episodes of abnormal respiration.

BRIEF DESCRIPTION OF THE DRAWINGS

The above and further features, advantages and benefits of the invention will be apparent upon consideration of the descriptions herein taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators are used to refer to like parts or elements throughout.

Overview of Implantable Medical System

Figure 1:
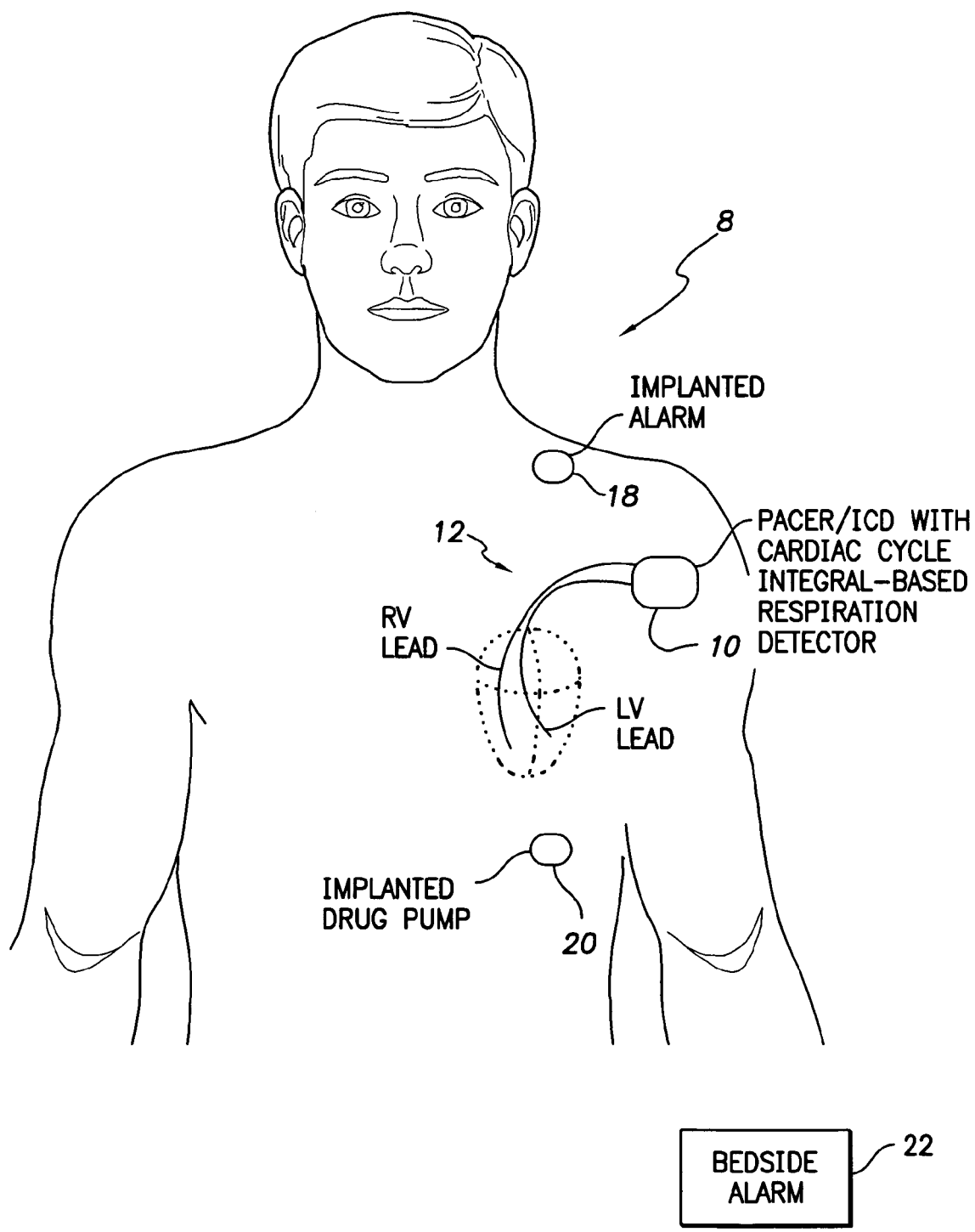
FIG. 1 illustrates pertinent components of an implantable medical system having a pacer/ICD capable of: tracking respiration patterns based on integrals of complete cycles of IEGM signals detected via leads mounted in the heart; detecting episodes of abnormal respiration based on the respiration patterns; and delivering therapy or warning signals in response thereto.

FIG. 1 illustrates an implantable medical system 8 having a pacer/ICD capable of tracking respiration based on integrals of complete cardiac cycles derived from IEGM signals, identifying episodes of abnormal respiration and delivering appropriate therapy. To this end, pacer/ICD 10 receives voltage signals from cardiac pacing leads 12 (only two of which are shown in the FIG. 1) from which IEGM signals are derived including, for example, unipolar or bipolar A-IEGM signals and unipolar or bipolar V-IEGM signals. A complete set of exemplary pacing leads are shown in FIG. 15 from which a wide variety of specific channels of IEGM signals may be derived. Based on the IEGM signals, the pacer/ICD detects patient respiration using techniques described below with reference to FIGS. 2-7. The pacer/ICD then also detects individual episodes of abnormal respiration, such as apnea, asthma or CSR, if occurring within the patient.

Once an episode of abnormal respiration has been detected, the pacer/ICD uses additional implanted components (if so equipped) to deliver appropriate therapy or warning signals. For example, if abnormal respiration is detected, the pacer/ICD may activate an internal alarm 18 or an external bedside alarm 22. Internal alarm 18 may be a vibrating device or a "tickle" voltage device that, in either case, provides perceptible stimulation to the patient to alert or awaken the patient so as to terminate the episode of abnormal respiration. The bedside alarm may provide audible or visual alarm signals of sufficient magnitude to alert or awaken the patient. If an activity sensor is provided within the pacer/ICD, the form of the alarm may be controlled based on patient activity. For example, if the activity level indicates that the patient is asleep, a more noticeable alarm may be employed than if the patient is deemed to be awake. In addition, while the patient is asleep, the intensity of the alarm signal can be periodically increased until the patient awakens, as detected by the activity sensor. Additionally, or in the alternative, the system may include a drug pump 20 capable of the delivering medications in an attempt to prevent the onset of additional episodes of abnormal respiration. Discussions of exemplary medications are provided below. In addition, the pacer/ICD may deliver atrial overdrive pacing for the purposes of preventing additional episodes of abnormal respiration from occurring, particularly apnea/hypopnea.

Thus, FIG. 1 provides an overview of an implantable system for tracking respiration, detecting episodes of abnormal respiration and for delivering therapy in response thereto. Although a pacer/ICD is illustrated in FIG. 1, it should be understood that the detection techniques of the invention may be implemented within other implantable devices, including dedicated respiration detection devices not necessarily capable of providing cardiac stimulation therapy. Note also that internal signal transmission lines for interconnecting the various implanted components are not shown. Alternatively, wireless signal transmission may be employed. Also, the particular locations of the implanted components are merely exemplary. In addition, it should be appreciated that systems provided in accordance with invention need not include all the components shown in FIG. 1. In many cases, for example, the system will include only the pacer/ICD and its leads. Other implementations will employ internal or external alarms but no drug pumps. These are just a few exemplary embodiments. No attempt is made herein to describe all possible combinations of components that may be provided in accordance with the general principles of the invention.

Figure 2:
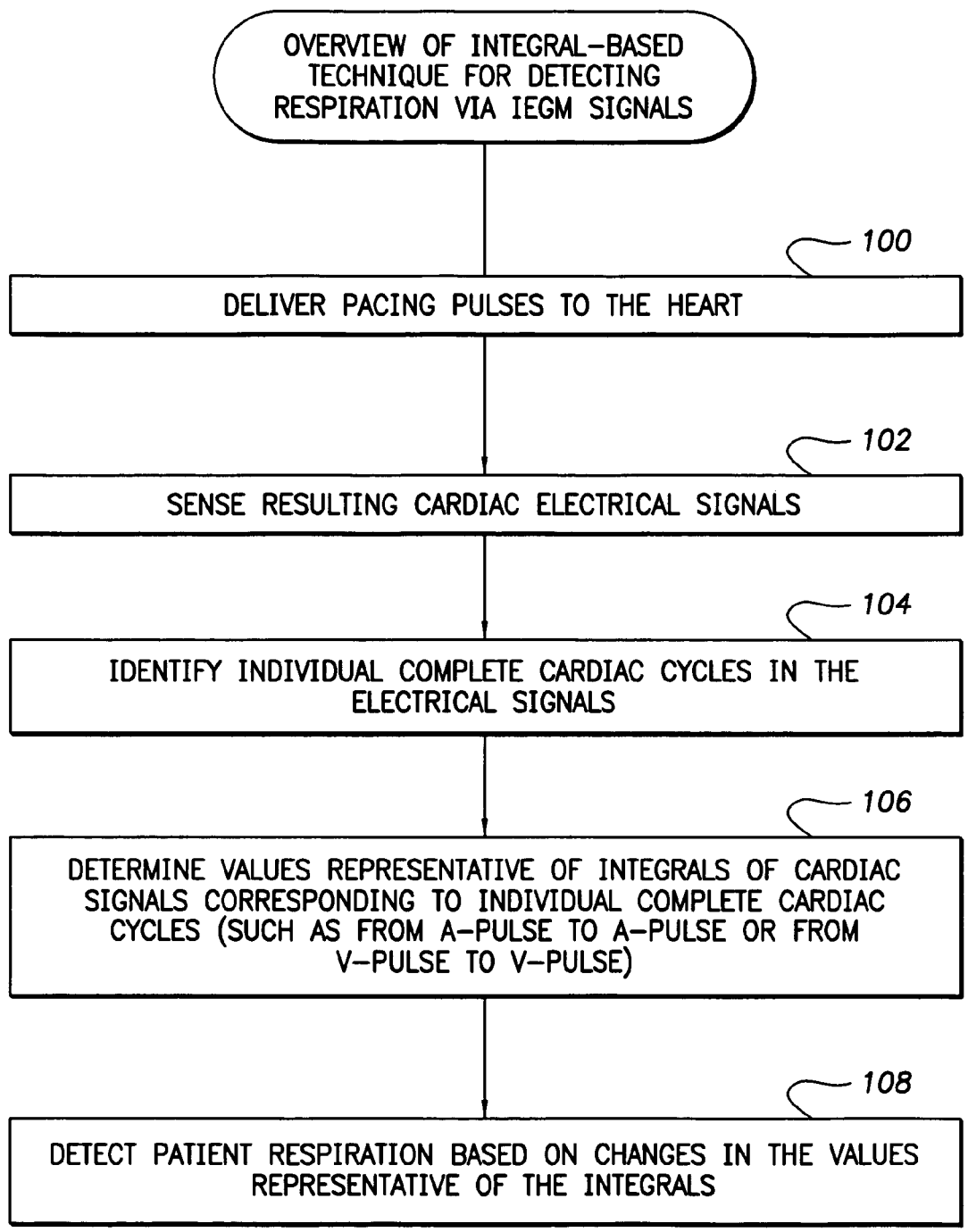
FIG. 2 is a flow chart providing an overview of the method for detecting patient respiration based on integrals of complete cycles of IEGM signals, which may be performed by the system of FIG. 1.

Technique for Detecting Respiration Based on Integrals of Complete Cardiac Cycles FIG. 2 provides an overview of the integral-based technique for detecting respiration via IEGM signals. Initially, at step 100, the pacer/ICD delivers pacing pulses to the heart in accordance with otherwise conventional cardiac pacing techniques. This may include delivery of atrial pacing pulses (A-pulses), ventricular pacing pulses (V-pulse), or both. At step 102, the pacer/ICD senses the resulting cardiac electrical signals, preferably in the form of an IEGM. At step 104, pacer/ICD identifies individual complete cardiac cycles within the electrical signals. In the case of atrial pacing, each individual complete cardiac cycle may be identified by tracking consecutive A-pulses, i.e. the interval from one A-pulse to the next A-pulse defines one complete cardiac cycle. This assumes, of course, that atrial pacing is continuous, i.e. the pacer/ICD is not performing demand-based atrial pacing wherein the device waits to determine if a P-wave is detected before delivering an A-pulse. For ventricular pacing, each individual complete cardiac cycle may be identified by tracking consecutive V-pulses. Again, this assumes that demand-based ventricular pacing is not the performed. If the atria and ventricles are both paced, then the pacer/ICD may choose to track cardiac cycles based either on consecutive A-pulses or on consecutive V-pulses. Potentially, other features of the cardiac signal may be used to detect and track individual complete cycles. However, tracking based upon consecutive like pacing pulses is convenient and expedient.

At step 106, the pacer/ICD determines values representative of the integrals of the cardiac signals corresponding to each individual complete cardiac cycle. In other words, the pacer/ICD integrates the electrical cardiac signals corresponding to each individual cardiac cycle to determine a separate integrated value for each cardiac cycle. If cardiac cycles are tracked from A-pulse to A-pulse, the pacer/ICD integrates the cardiac signals between each pair of consecutive A-pulses. If cardiac cycles are instead tracked from V-pulse to V-pulse, the pacer/ICD integrates the cardiac signals between each pair of consecutive V-pulses. At step 108, the pacer/ICD detects patient respiration based on the values representative of the integrals. In this regard, it is believed that the displacement of the IEGM sensing electrodes caused by movement of the thorax during respiration causes slight variations in the shape of the IEGM signal sufficient to induce variations in the integral of the IEGM signals. Otherwise conventional filters may be used to isolate patterns appearing at frequencies associated with respiration. Based on these variations, the pacer/ICD detects at least one parameter associated with respiration. Typically, the pacer/ICD detects the number of respiration cycles per minute and/or detects a value generally representative of the depth of respiration, i.e. the amount of air being inhaled and exhaled. Based upon these gross parameters of respiration, the pacer/ICD can then detect episodes of abnormal respiration, which is discussed in greater detail below with reference to the FIG. 8.

Insofar as integrating the individual cardiac cycles is concerned, in one example, integration is performed by summing the absolute values of all the individual samples of the electrical cardiac signal within each complete cardiac cycle. Calculating the absolute value of the individual samples of the electrical cardiac signal prior to integration or summation is only necessary if the individual samples include negative as well as positive values. However, typically, pacer/ICDs include an analog-to-digital converter (ADC), which converts input electrical cardiac signals into digital numerical values having only positive values. Hence, separately calculating the absolute value of the individual samples is usually not necessary.

Figure 3:
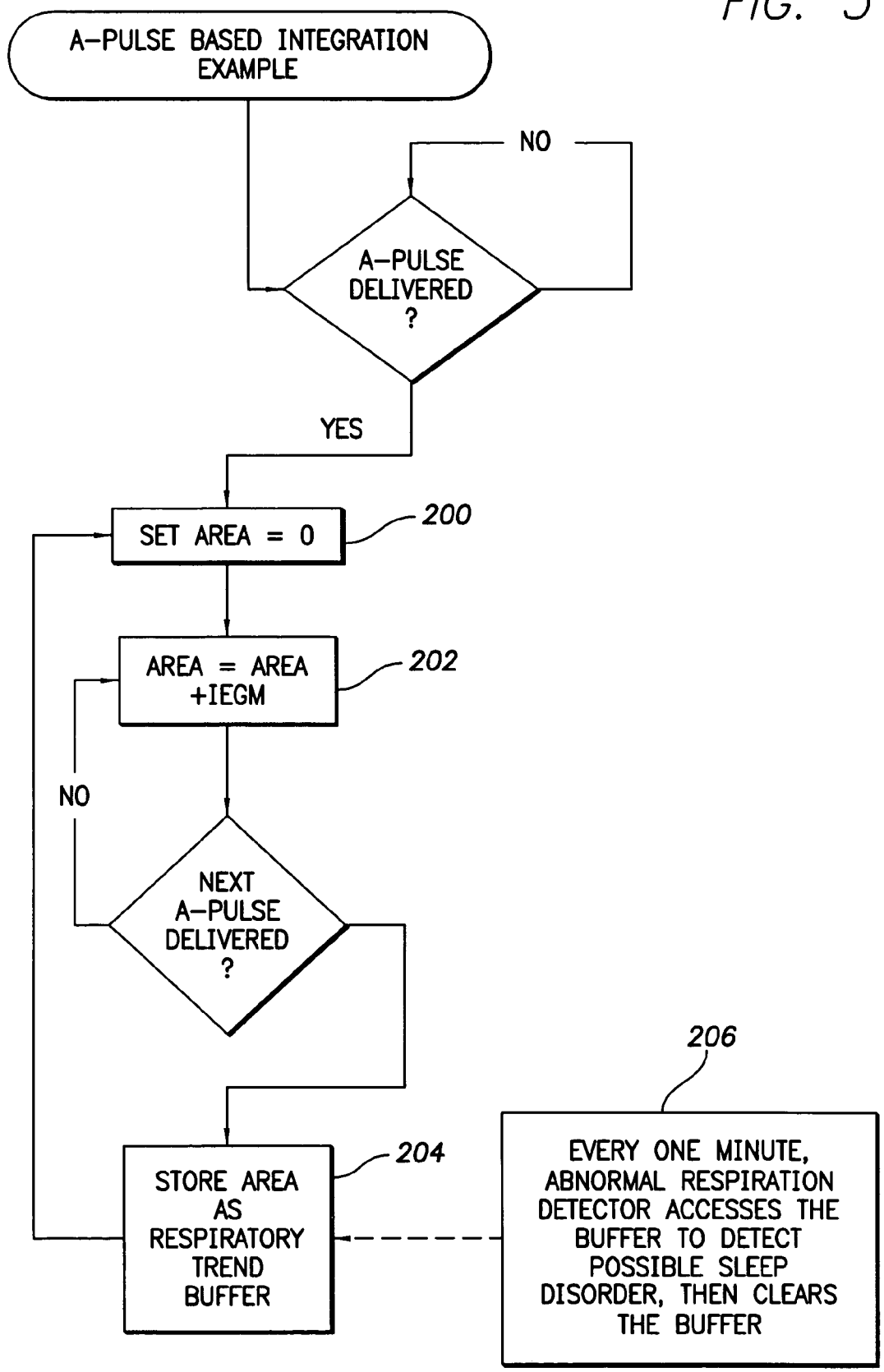
FIG. 3 is a flow chart providing an exemplary technique for calculating the integrals based on atrial paced cardiac signals, which may be performed by the system of FIG. 1.
Figure 4:
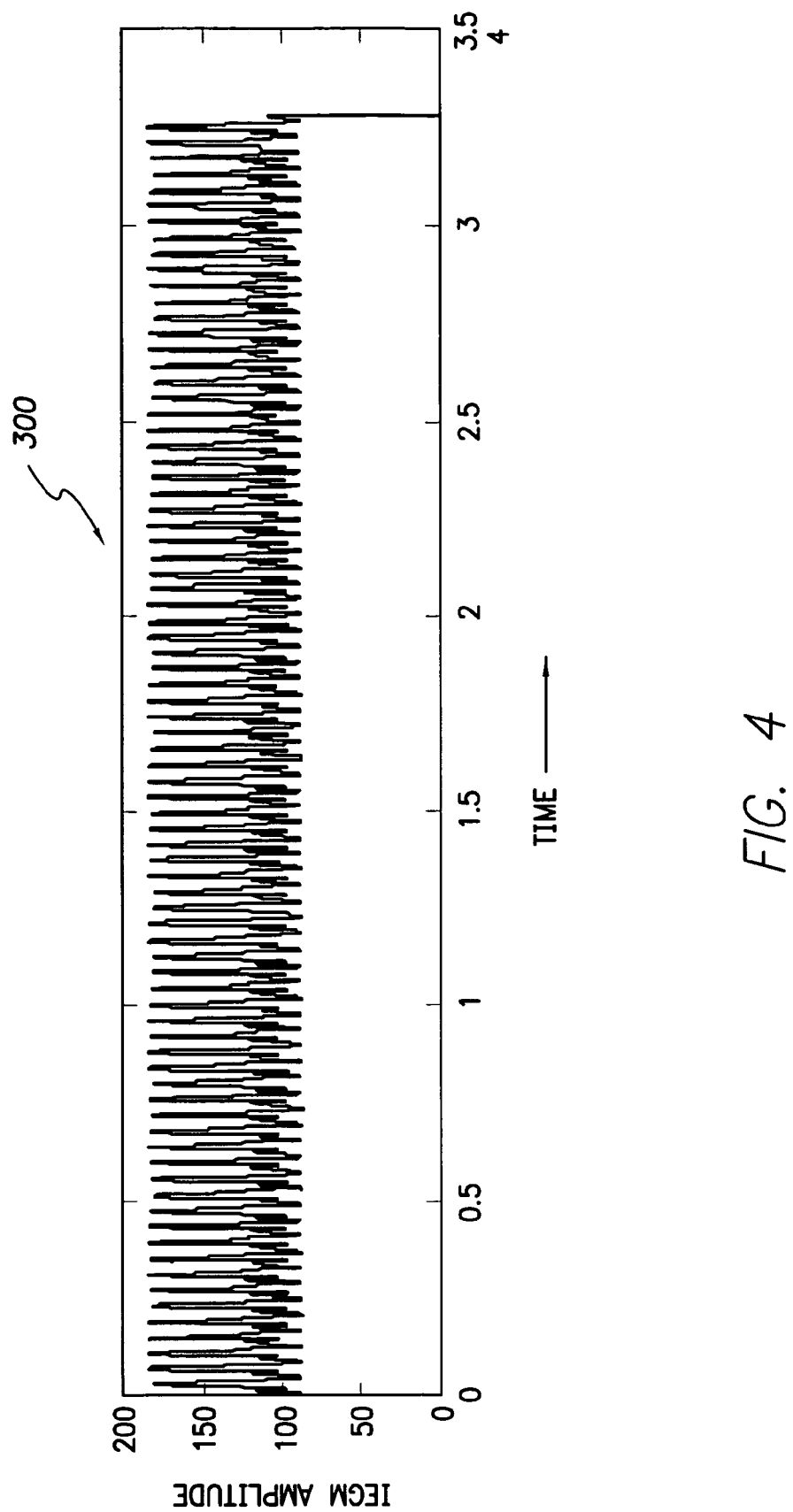
FIG. 4 is a graph illustrating exemplary IEGM data, which may be analyzed via the method of FIG. 2.

A specific technique for calculating the integrals for an example involving atrial pacing is illustrated in FIG. 3. At step 200, an "area" value is set to zero. The area value will ultimately be representative of the area under the curve defined by the digital samples of electrical cardiac signals for an individual cardiac cycle. In other words, the area value, once fully calculated, corresponds to the integral. At step 202, the area value is updated to add the value of a new digital sample of the IEGM, i.e. the latest digital sample of the IEGM derived from the ADC is added to the previous value of the area. This example assumes that output values from ADC are all positive so that the absolute value need not be calculated. Assuming the next A-pulse has not yet been delivered, then step 202 is repeated to add the value of another new digital sample of the IEGM to the previous value of the area. Step 202 is repeated in a loop until all digital samples corresponding to the current complete cardiac cycle are summed. The delivery of the next A-pulse marks the beginning of the next cardiac cycle. Accordingly, once a next A-pulse is delivered, then step 204 is performed wherein the final value of the area is stored in a respiratory trend buffer. Processing then returns to step 200, where "area" is reset to zero for use in summing the digital samples of the IEGM for the next complete cardiac cycle. Processing continues in this manner to calculate and store a new area value within the trend buffer for each cardiac cycle. Hence, assuming the heart of the patient is beating about 60 beats per minute (bpm), about 60 values are calculated and stored per minute. Hence, the trend buffer stores an entire sequence of area values, each having slightly different numerical values. Cyclical patterns exhibited by the sequence of area values are representative of respiration. If the area values stored in the trend buffer do not exhibit any significant variation over some predetermined period of time, then a respiration disorder has likely occurred, such as apnea.

Meanwhile, step 206 is performed once every minute (or other designated period of time) wherein an abnormal respiration detector accesses the trend buffer to examine the area value stored therein to detect a possible respiration disorder, such as apnea. Once the analysis complete, the trend buffer is cleared. To detect respiration disorders such as CSR that exhibit patterns extending over a greater period of time, step 206 is performed less frequently so as to permit analysis of a greater amount of trend buffer data.

Figure 5:
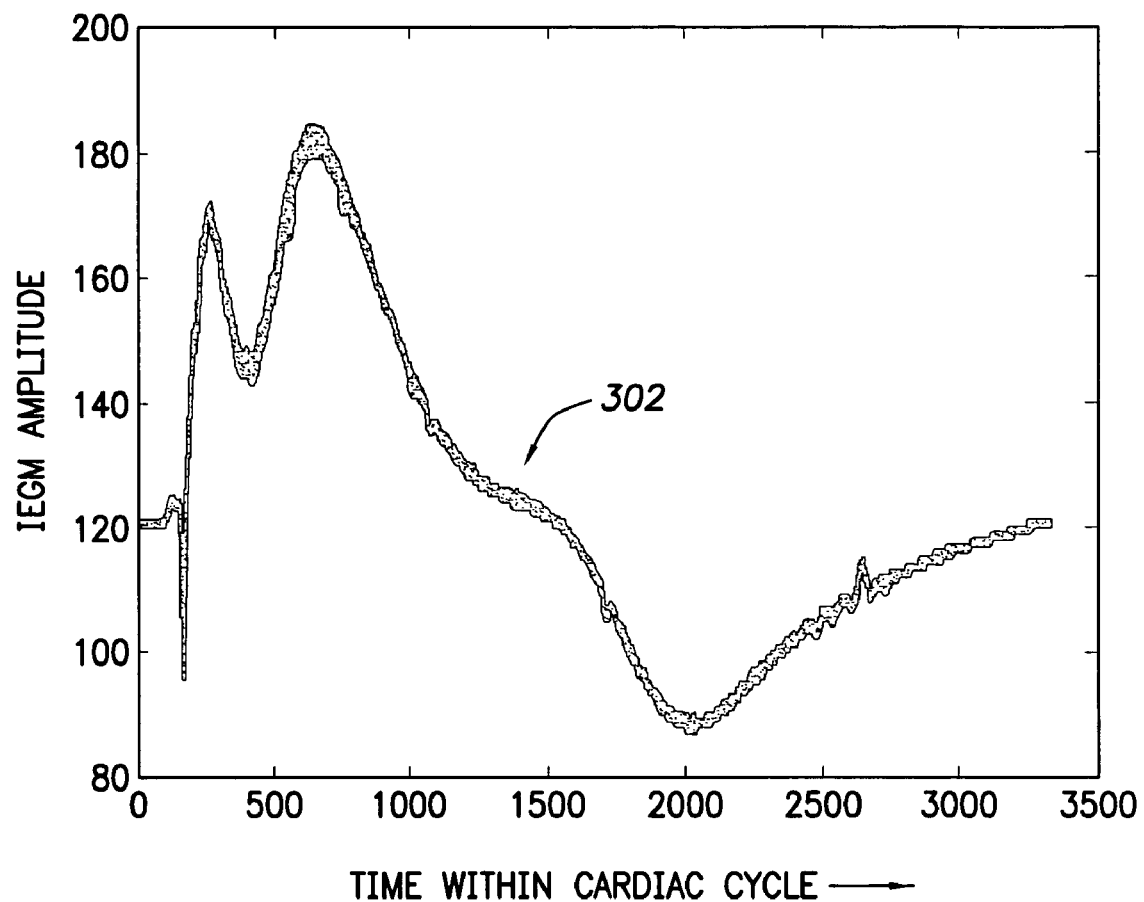
FIG. 5 is a graph illustrating the IEGMs of the individual cardiac cycles of FIG. 4 superimposed on one another, and particularly illustrating variations in IEGM morphology due to patient respiration.

Specific examples are illustrated in FIGS. 4-7. Within FIG. 4, an exemplary paced ventricular IEGM 300 is illustrated over about sixty cardiac cycles. The V-pulses are not separately shown. The vertical scale is representative of the voltage or amplitude of the IEGM shown on an arbitrary numerical scale. The horizontal scale, which is representative of time, is likewise on an arbitrary scale. FIG. 5 illustrates the IEGM patterns 302 of the individual cardiac cycles of FIG. 4 superimposed on one another so as to highlight slight variations in the IEGM patterns. The vertical scale is again representative of the voltage or amplitude of the IEGM, shown on the same arbitrary numerical scale. The horizontal scale is representative of time tracked from the beginning of the cardiac cycle, again shown on an arbitrary scale. The cardiac cycle begins with delivery of a V-pulse (not separately shown). As can be seen, there are slight variations in the shape of the IEGM patterns. These slight variations allow extraction of respiratory parameters.

Figure 6:
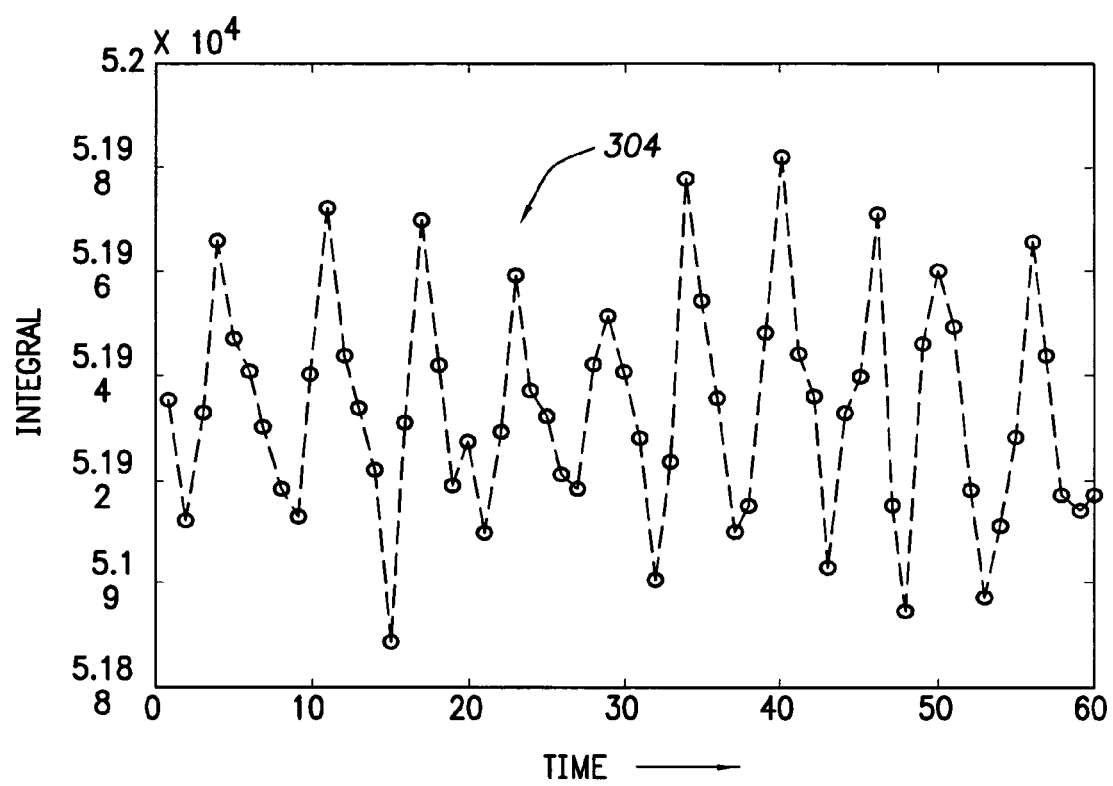
FIG. 6 is a graph illustrating a first exemplary respiration pattern derived using the integral-based method of FIG. 2.
Figure 7:
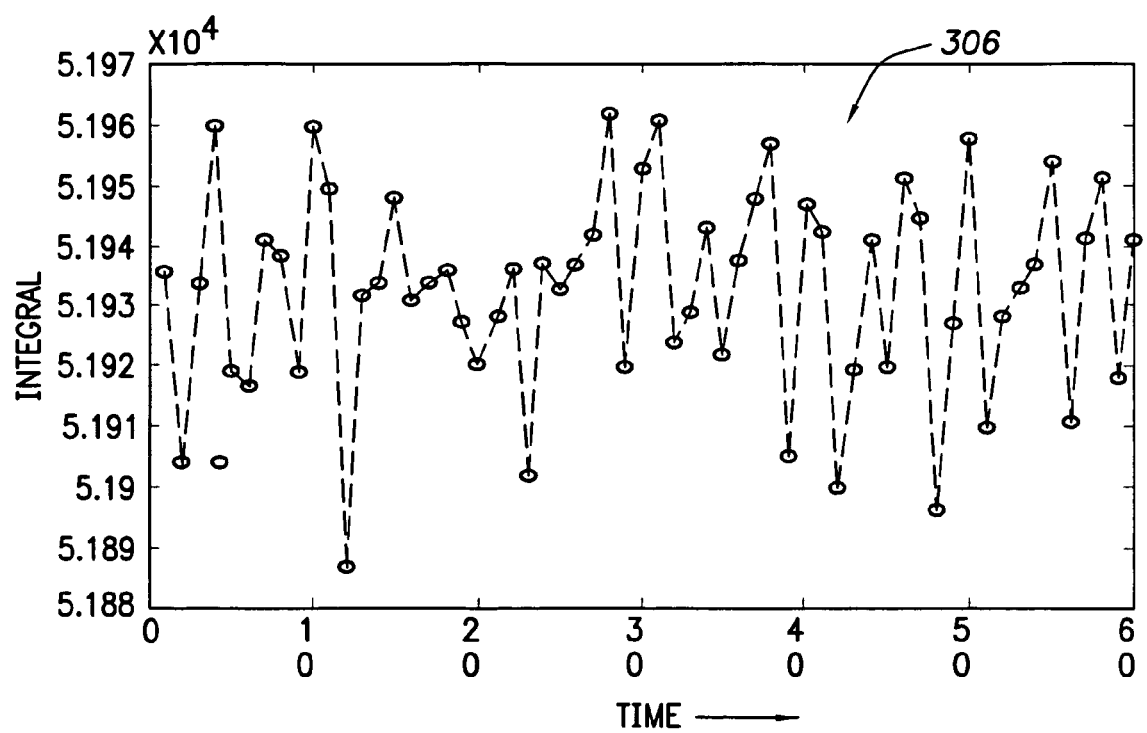
FIG. 7 is a graph illustrating a second exemplary respiration pattern derived using the integral-based method of FIG. 2.

Turning now to FIG. 6, a first exemplary respiration pattern 304 is illustrated. The respiration pattern was derived from the data of FIG. 5, by using the technique of FIG. 2. Each individual circle within FIG. 6 corresponds to the area or integral value for one individual cardiac cycle of the superimposed cardiac cycles of FIG. 5. A dashed line is shown interconnecting the circles to more clearly illustrate the cyclical patterns exhibited by the data, which are representative of the gross features of respiration such as respiration period. The vertical scale represents the numerical value of the integrals. The horizontal scale represents time, over a period of about 60 seconds. A second example is illustrated by way of graph 306 of FIG. 7, which illustrates another respiration pattern derived from other data. The vertical scale again represents the numerical value of the integrals. The horizontal scale again represents time. The gross features of respiration are again quite evident. Note that neither of the exemplary respiration patterns precisely tracks actual patient respiration (which tends to be more smoothly sinusoidal). Nevertheless, the presence of the cyclical pattern is at least indicative of ongoing respiration. The lack of any significant cyclical variation in the data would instead be indicative of a lack of respiration as in, e.g. apnea/hypopnea. Hence, respiration patterns detected using the techniques of invention are at least sufficient for the purposes of detecting significant respiration disorders. Alternative respiration detection techniques may be employed to corroborate any respiration disorders detected using the techniques invention. See, for example, the respiration detection techniques set forth in the patents cited above of Park, Andersson and Bharmi.

Abnormal Respiration Detection and Therapy

Figure 8:
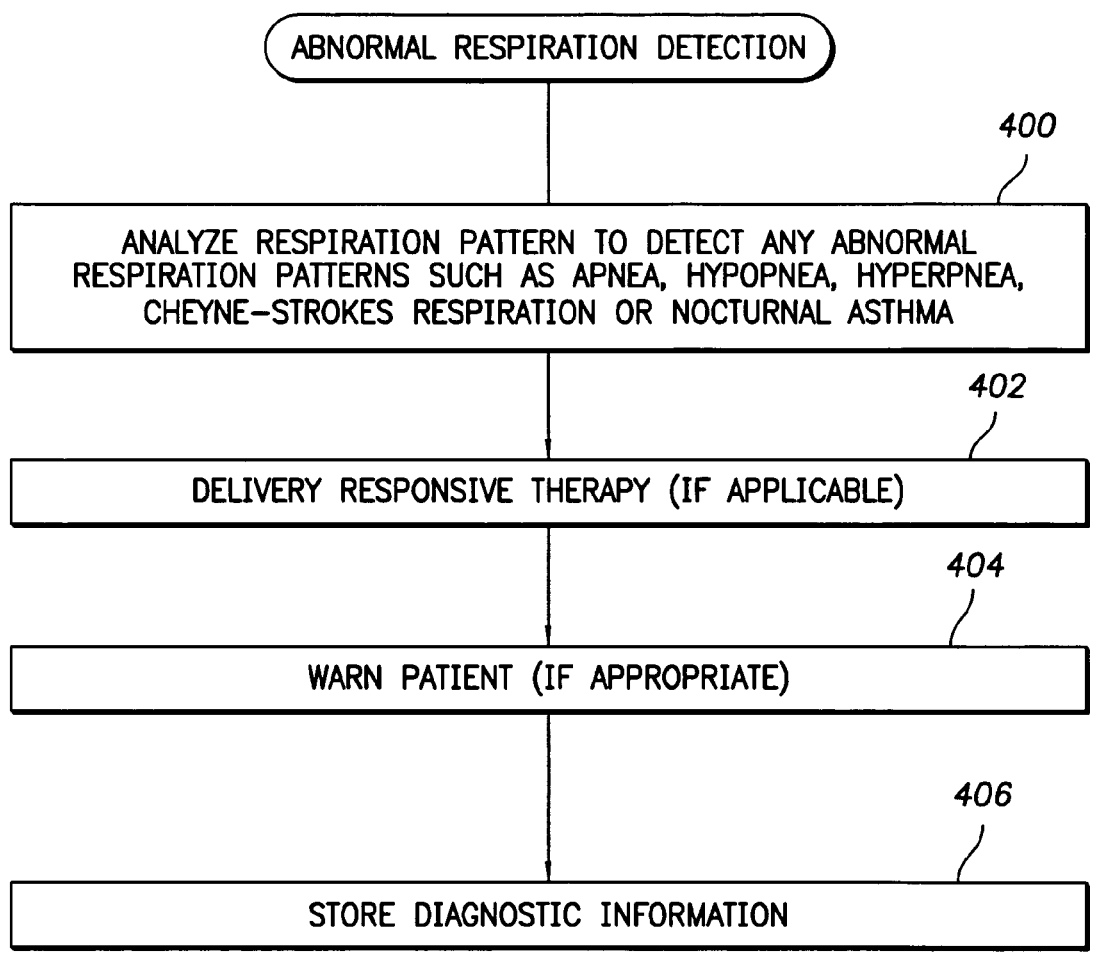
FIG. 8 is a flow chart illustrating abnormal respiration detection techniques, which may be performed by the system of FIG. 1, based on respiration patterns detecting using the techniques of FIG. 2.

What have been described thus far are various techniques for tracking respiration patterns based on features of IEGM signals. With reference to FIG. 8, techniques for detecting episodes of abnormal respiration based on the respiration patterns and delivering therapy will now be more thoroughly described. At step 400, the pacer/ICD analyzes the detected respiration pattern to detect episodes of abnormal respiration such as apnea and hypopnea, hyperpnea, nocturnal asthma, and CSR, based on respiration rate and/or amplitude. In general, otherwise conventional techniques for detecting episodes of abnormal respiration, which use respiration rates or respiration amplitudes, may be employed.

Briefly, apnea may be detected based upon a lack of any significant amplitude variations within the detected respiration patterns extending over a predetermined period of time. In one example, an apnea detection amplitude threshold value may be specified along with an apnea detection time threshold value. If the respiratory amplitude derived from the respiration patterns does not exceed the amplitude threshold value for at least a period of time greater than the time threshold value, then apnea is presumed. Typically, an episode of apnea is not deemed to have occurred unless there is a lack respiration for at least ten seconds and so a time threshold of at least ten seconds may be employed. A suitable amplitude threshold value may be determined via routine experimentation for use with respiration patterns derived from particular IEGM parameters. The values may also differ from patient to patient. Suitable threshold values may be specified following implant of device based on the specific characteristics of patient in which the device is implanted. More complex techniques may alternatively be employed for identifying an episode of apnea.

Hypopnea may be detected based upon respiratory amplitude that exceeds the apnea threshold but falls below a separate hypopnea amplitude threshold. As with apnea, a time threshold value (such as one minute) may be specified as well. Hence, if there is at least some respiration, but the amplitude of that respiration falls below an amount deemed healthy for the patient, hypopnea is presumed. As with the various apnea thresholds, separate hypopnea threshold values may specified for use with different patients, preferably determined on a patient by patient basis following implant of the device. Alternative and more complex hypopnea detection techniques may be employed as well.

Hyperpnea/asthma may be detected based upon a pattern exhibiting excessively rapid respiration (or attempted respiration.) Accordingly, a hyperpnea/asthma amplitude detection threshold may be specified along with a hyperpnea/asthma respiration rate threshold. If amplitude derived from the respiration pattern exceeds the hyperpnea/asthma respiration amplitude detection threshold while the respiration rate (also derived from the respiration pattern) also exceeds it respective threshold, hyperpnea/asthma is thereby presumed. Again, suitable thresholds may be determined on the patient basis following implant of device. Alternative and more complex hyperpnea/asthma or CSR detection techniques may be employed as well.

Hyperpnea usually may be distinguished from asthma based on the presence or absence of normal respiration preceding the attack. Hyperpnea usually follows an episode of apnea/hypopnea; whereas asthma usually follows a period of otherwise normal breathing. Episodes of nocturnal asthma may be distinguished from other asthma attacks merely by determining whether the patient is asleep, using otherwise conventional sleep detection techniques. Examples of sleep detection techniques are set forth in: U.S. Pat. No. 5,476,483, to Bornzin et al., entitled "System and Method for Modulating the Base Rate During Sleep for a Rate-responsive Cardiac Pacemaker" and U.S. Pat. No. 6,128,534 to Park et al., entitled "Implantable Cardiac Stimulation Device and Method for Varying Pacing Parameters to Mimic Circadian Cycles."

CSR may be detected using otherwise conventional techniques based on its characteristic pattern of alternating periods of apnea/hypopnea and hyperpnea. See, e.g., U.S. Pat. No. 6,830,548 to Bonnet et al., "Active Medical Device Able to Diagnose a Patient Respiratory Profile." To detect CSR trend data extending over at least several minutes is preferably employed.

Once an episode of abnormal respiration has been detected then, at step 402, the pacer/ICD delivers appropriate therapy (assuming it is properly equipped). For example, in response to detection of frequent episodes of apnea/hypopnea, atrial overdrive pacing therapy may be applied in an attempt to prevent the onset of additional episodes. A particularly effective atrial overdrive pacing technique, referred to herein as dynamic atrial overdrive (DAO) pacing, is described in U.S. Pat. No. 6,519,493 to Florio et al., entitled "Methods and Apparatus for Overdrive Pacing Heart Tissue Using an Implantable Cardiac Stimulation Device." Routine experimentation may be performed to identify optimal DAO pacing parameters for use with patients with apnea/hypopnea. The aggressiveness of DAO therapy may be adjusted based upon the frequency or duration of episodes of apnea/hypopnea.

Anti-apneic medications may be delivered via an implantable drug pump, if so equipped. Examples of medications that may be helpful in patients with apnea are set forth the following patents: U.S. Pat. No. 6,331,536 to Radulovacki et al., entitled "Pharmacological Treatment for Sleep Apnea"; U.S. Pat. No. 6,432,956 to Dement et al., entitled "Method for Treatment of Sleep Apneas"; U.S. Pat. No. 6,586,478 to Ackman et al., entitled "Methods and Compositions for Improving Sleep"; and U.S. Pat. No. 6,525,073 to Mendel et al., entitled "Prevention or Treatment of Insomnia with a Neurokinin-1 Receptor Antagonist." Depending upon the particular medication, alternative compounds may be required for use in connection with an implantable drug pump. Routine experimentation may be employed to identify medications for treatment of sleep apnea that are safe and effective for use in connection with an implantable drug pump. Dosages may be titrated based upon the frequency or duration of episodes of apnea.

During the actual episode of apnea/hypopnea, an implantable alarm (such as alarm 18 of FIG. 1) may be activated to awaken the patient (assuming the patient is sleeping) in an attempt to terminate the episode of apnea/hypopnea. Alternatively, a bedside alarm may be activated by transmission of appropriate wireless control signals. Activation of an alarm to awaken the patient is preferably employed only if other therapy is found to be ineffective, since awakening the patient interrupts with the patient's natural sleeping patterns. In any case, whenever some form of apnea/hypopnea therapy is delivered, appropriate diagnostic information is stored (at step 406) so that if medical professional can subsequently review the therapy and evaluate its effectiveness.

If implantable phrenic nerve stimulators are implanted, apnea/hypopnea therapy can also involve delivery of rhythmic electrical stimulation to the phrenic nerves to mimic breathing (assuming the apnea/hypopnea is due to a lack of phrenic nerve signals.) Examples of phrenic nerve stimulators are set forth in U.S. Pat. No. 5,056,519 to Vince, entitled "Unilateral Diaphragmatic Pacer" and in U.S. Pat. No. 6,415, 183 to Scheiner et al., entitled "Method and Apparatus for Diaphragmatic Pacing," which are incorporated by reference herein. Other respiratory nerves may be stimulated as well. U.S. Pat. No. 5,911,218 to DiMarco, entitled "Method and Apparatus for Electrical Stimulation of the Respiratory Muscles to Achieve Artificial Ventilation in a Patient" describes stimulation of nerves leading to intercostal muscles.

If an implantable hypoglossyl nerve stimulator is implanted, therapy can also involve delivery of stimulation to the hypoglossyl nerves in response to obstructive sleep apnea. Examples of hypoglossyl nerve stimulators are set forth in U.S. Patent Application 2003/0216789 of Deem et al., entitled "Method and System for Treating Sleep Apnea."

Insofar as CSR therapy is concerned, CSR often arises due to CHF and so CSR can often be remedied by addressing the underlying CHF. See, e.g. U.S. patent application Ser. No. 10/792,305, filed Mar. 2, 2004, entitled "System and Method for Diagnosing and Tracking Congestive Heart Failure Based on the Periodicity of Cheyne-Stokes Respiration Using an Implantable Medical Device"; and U.S. patent application Ser. No. 10/792,305, filed Mar. 2, 2004, entitled "System and Method for Diagnosing and Tracking Congestive Heart Failure Based on the Periodicity of Cheyne-Stokes Respiration Using an Implantable Medical Device". Accordingly, upon detection of episodes CSR, the pacer/ICD preferably employs otherwise conventional techniques to detect CHF and, if CHF is present, any of a variety of therapies directed to mitigating CHF may be implemented by the device. For example, cardiac resynchronization therapy (CRT) may be performed to improve cardiac function. CRT and related therapies are discussed in, for example, U.S. Pat. No. 6,643, 546 to Mathis et al., entitled "Multi-Electrode Apparatus and Method for Treatment of Congestive Heart Failure"; U.S. Pat.

No. 6,628,988 to Kramer et al., entitled "Apparatus and Method for Reversal of Myocardial Remodeling With Electrical Stimulation"; and U.S. Pat. No. 6,512,952 to Stahmann et al., entitled "Method and Apparatus for Maintaining Synchronized Pacing." CHF therapy may also include delivery of medications via an implantable drug pump, if so equipped. Exemplary CHF medications include ACE inhibitors, diuretics, digitalis and compounds such as captopril, enalapril, lisinopril and quinapril. Depending upon the particular medication, alternative compounds may be required for use in connection with an implantable drug pump. Routine experimentation may be employed to identify medications for treatment of CHF that are safe and effective for use in connection with an implantable drug pump.

Additionally, during an individual episode of CSR, the implantable alarm or external bedside alarm may be triggered to awaken the patient to break the cycle of CSR. Again, activation of an alarm to awaken the patient is preferably employed only if other forms of therapy are found to be ineffective. See, also, U.S. patent application Ser. No. 10/844, 023, filed May 11, 2004, entitled "System and Method for Providing Demand-Based Cheyne-Stokes Respiration Therapy Using an Implantable Medical Device".

Insofar as hyperpnea is concerned, hyperpnea may arise during CSR or may arise during an asthma attack. Hyperpnea arising due to CSR is preferably addressed via CSR therapy. See, also, U.S. patent application Ser. No. 10/829,719, filed Apr. 21, 2004, entitled "System and Method for Applying Therapy during Hyperpnea Phase of Periodic Breathing Using an Implantable Medical Device". Hyperpnea arising due to asthma may be addressed by addressing the asthma via suitable medications delivered via the implantable drug pump. Examples of asthma medications are set forth, for example, in U.S. Pat. No. 4,089,959 to Diamond, entitled "Long-Acting Xanthine Bronchodilators and Antiallergy Agents." Depending upon the particular medication, alternative compounds may be required for use in connection with an implantable drug pump. Routine experimentation may be employed to identify medications for treatment of asthma that are safe and effective for use in connection with an implantable drug pump. Dosages may be titrated as needed based on tracking and trending of such breathing patterns.

Additional techniques may be used, if desired, to corroborate the detection of an episode of abnormal respiration made using the techniques of the invention before therapy is delivered. See, e.g., U.S. patent application Ser. No. 10/883,857, filed Jun. 30, 2004, entitled "System and Method For Real-Time Apnea/Hypopnea Detection Using An Implantable Medical System and U.S. patent application Ser. No. 10/821, 241, filed Apr. 7, 2004, entitled "System And Method For Apnea Detection Using Blood Pressure Detected via an Implantable Medical System".

Continuing with FIG. 8, at step 404, suitable warning signals may be delivered to alert the patient, his/her physician or other medical personnel to any episodes of abnormal breathing. At step 406, diagnostic information pertaining to episodes of abnormal respiration and any therapy applied, is stored for subsequent review.

What have been described are various techniques for tacking respiration via IEGM signals, detecting episodes of abnormal respiration and delivering appropriate therapy. For the sake of completeness, a detailed description of an exemplary pacer/ICD for controlling these functions will now be provided. However, principles of invention may be implemented within other pacer/ICD implementations or within other implantable devices.

Pacemaker/ICD

Figure 9:
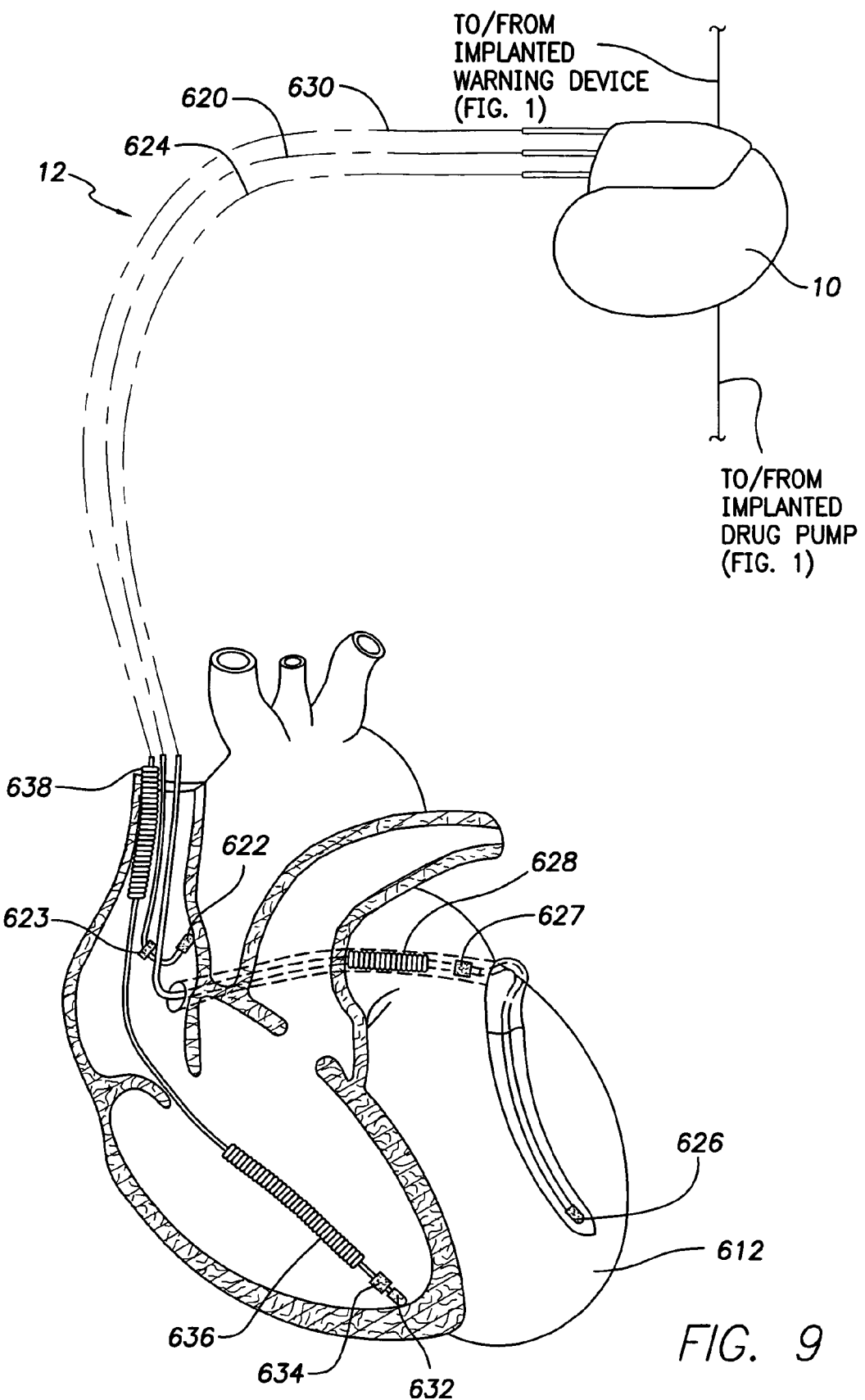
FIG. 9 is a simplified, partly cutaway view, illustrating the pacer/ICD of FIG. 1 along with a complete set of leads implanted in the heart of a patient.

FIG. 9 provides a simplified block diagram of the pacer/ICD, which is a multi-chamber stimulation device capable of treating both fast and slow arrhythmias with stimulation therapy, including cardioversion, defibrillation, and pacing stimulation (as well as capable of tracking respiration, detecting episodes of abnormal respiration and delivering appropriate therapy.) To provide atrial chamber pacing stimulation and sensing, pacer/ICD 10 is shown in electrical communication with a heart 612 by way of a left atrial lead 620 having an atrial tip electrode 622 and an atrial ring electrode 623 implanted in the atrial appendage. Pacer/ICD 10 is also in electrical communication with the heart by way of a right ventricular lead 630 having, in this embodiment, a ventricular tip electrode 632, a right ventricular ring electrode 634, a right ventricular (RV) coil electrode 636, and a superior vena cava (SVC) coil electrode 638. Typically, the right ventricular lead 630 is transvenously inserted into the heart so as to place the RV coil electrode 636 in the right ventricular apex, and the SVC coil electrode 638 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 624 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 624 is designed to receive atrial and ventricular cardiac signals and to deliver left ventricular pacing therapy using at least a left ventricular tip electrode 626, left atrial pacing therapy using at least a left atrial ring electrode 627, and shocking therapy using at least a left atrial coil electrode 628. With this configuration, biventricular pacing can be performed. Although only three leads are shown in FIG. 9, it should also be understood that additional stimulation leads (with one or more pacing, sensing and/or shocking electrodes) may be used in order to efficiently and effectively provide pacing stimulation to the left side of the heart or atrial cardioversion and/or defibrillation. The leads are also employed for sensing ID tag signals from medications equipped with active ID transmitters.

Figure 10:
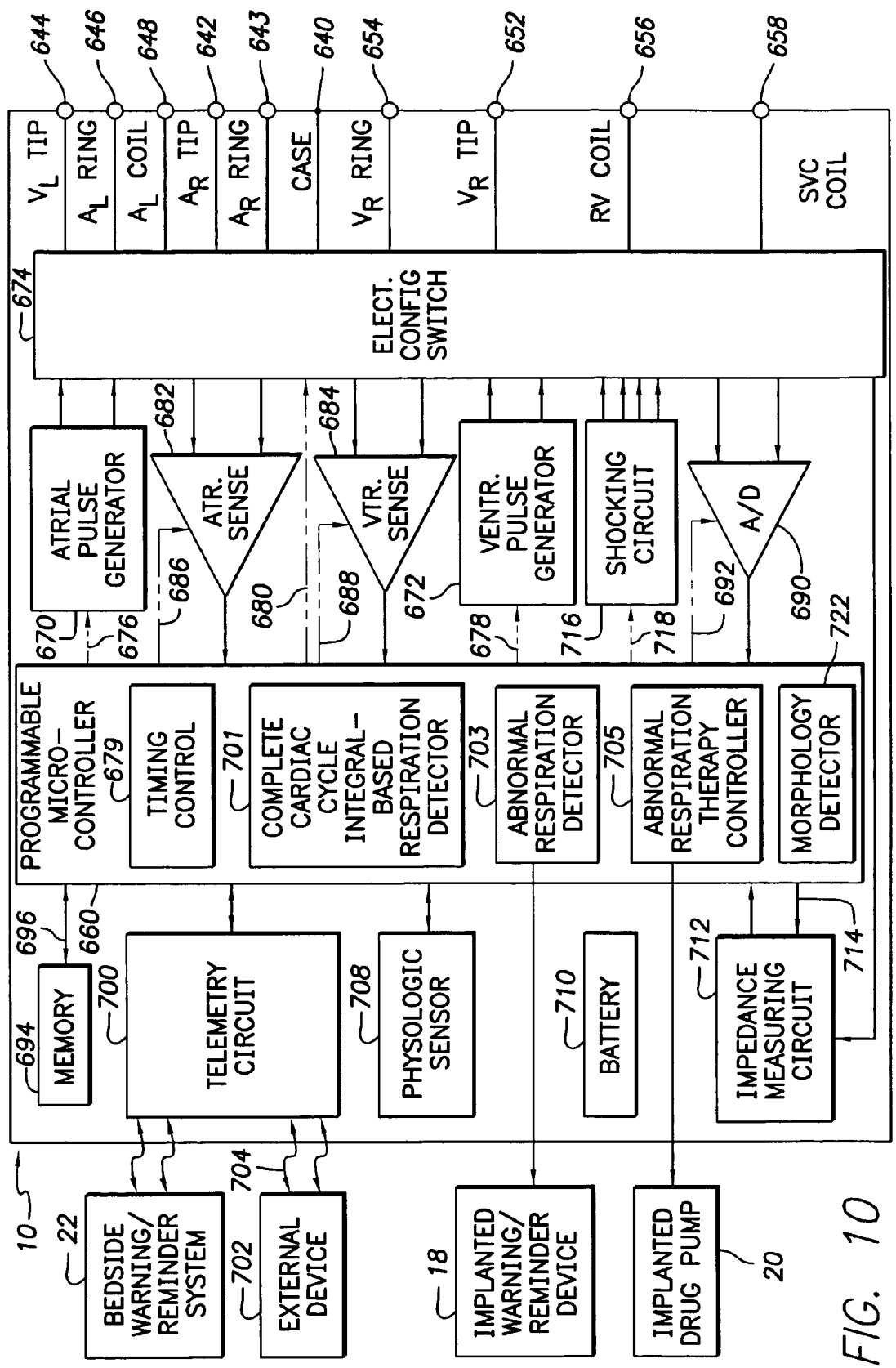
FIG. 10 is a functional block diagram of the pacer/ICD of FIG. 9, illustrating basic circuit elements that provide cardioversion, defibrillation and/or pacing stimulation in four chambers of the heart and particularly illustrating a complete cardiac cycle integral-based respiration detector, a abnormal respiration detector, and an abnormal respiration therapy controller.

A simplified block diagram of internal components of pacer/ICD 10 is shown in FIG. 10. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy. The housing 640 for pacer/ICD 10, shown schematically in FIG. 10, is often referred to as the "can", "case" or "case electrode" and may be programmably selected to act as the return electrode for all "unipolar" modes. The housing 640 may further be used as a return electrode alone or in combination with one or more of the coil electrodes, 628, 636 and 638, for shocking purposes. The housing 640 further includes a connector (not shown) having a plurality of terminals, 642, 643, 644, 646, 648, 652, 654, 656 and 658 (shown schematically and, for convenience, the names of the electrodes to which they are connected are shown next to the terminals). As such, to achieve right atrial sensing and pacing, the connector includes at least a right atrial tip terminal ($A_R$ TIP) 642 adapted for connection to the atrial tip electrode 622 and a right atrial ring ($A_R$ RING) electrode 643 adapted for connection to right atrial ring electrode 643. To achieve left chamber sensing, pacing and shocking, the connector includes at least a left ventricular tip terminal ($V_L$ TIP) 644, a left atrial ring terminal ($A_L$ RING) 646, and a left atrial shocking terminal ($A_L$ COIL) 648, which are adapted for connection to the left ventricular ring electrode 626, the left atrial tip electrode 627, and the left atrial coil electrode 628, respectively. To support right chamber sensing, pacing and shocking, the connector further includes a right ventricular tip terminal ($V_R$ TIP) 652, a right ventricular ring terminal ($V_R$ RING) 654, a right ventricular shocking terminal ($R_V$ COIL) 656, and an SVC shocking terminal (SVC COIL) 658, which are adapted for connection to the right ventricular tip electrode 632, right ventricular ring electrode 634, the $R_V$ coil electrode 636, and the SVC coil electrode 638, respectively. Separate terminals (not shown) may be provided for connecting the implanted warning/reminder device 18 and the implanted drug pump 20, which are instead shown coupled directly to internal functional components of the pacer/ICD that control these devices.

At the core of pacer/ICD 10 is a programmable microcontroller 660, which controls the various modes of stimulation therapy. As is well known in the art, the microcontroller 660 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 660 includes the ability to process or monitor input signals (data) as controlled by a program code stored in a designated block of memory. The details of the design and operation of the microcontroller 660 are not critical to the invention. Rather, any suitable microcontroller 660 may be used that carries out the functions described herein. The use of microprocessor-based control circuits for performing timing and data analysis functions are well known in the art.

As shown in FIG. 10, an atrial pulse generator 670 and a ventricular/impedance pulse generator 672 generate pacing stimulation pulses for delivery by the right atrial lead 620, the right ventricular lead 630, and/or the coronary sinus lead 624 via an electrode configuration switch 674. It is understood that in order to provide stimulation therapy in each of the four chambers of the heart, the atrial and ventricular pulse generators, 670 and 672, may include dedicated, independent pulse generators, multiplexed pulse generators or shared pulse generators. The pulse generators, 670 and 672, are controlled by the microcontroller 660 via appropriate control signals, 676 and 678, respectively, to trigger or inhibit the stimulation pulses.

The microcontroller 660 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 674 includes a plurality of switches for connecting the desired electrodes to the appropriate I/O circuits, thereby providing complete electrode programmability. Accordingly, the switch 674, in response to a control signal 680 from the microcontroller 660, determines the polarity of the stimulation pulses (e.g., unipolar, bipolar, combipolar, etc.) by selectively closing the appropriate combination of switches (not shown) as is known in the art.

Atrial sensing circuits 682 and ventricular sensing circuits 684 may also be selectively coupled to the right atrial lead 620, coronary sinus lead 624, and the right ventricular lead 630, through the switch 674 for detecting the presence of cardiac activity in each of the four chambers of the heart. Accordingly, the atrial (ATR. SENSE) and ventricular (VTR. SENSE) sensing circuits, 682 and 684, may include dedicated sense amplifiers, multiplexed amplifiers or shared amplifiers. The switch 674 determines the "sensing polarity" of the cardiac signal by selectively closing the appropriate switches, as is also known in the art. In this way, the clinician may program the sensing polarity independent of the stimulation polarity. Each sensing circuit, 682 and 684, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 682 and 684, are connected to the microcontroller 660 which, in turn, are able to trigger or inhibit the atrial and ventricular pulse generators, 670 and 672, respectively, in a demand fashion in response to the absence or presence of cardiac activity in the appropriate chambers of the heart.

For arrhythmia detection, pacer/ICD 10 utilizes the atrial and ventricular sensing circuits, 682 and 684, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 660 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 690. The data acquisition system 690 is configured to acquire intracardiac electrogram signals, convert the raw analog data into a digital signal, and store the digital signals for later processing and/or telemetric transmission to an external device 702. The data acquisition system 690 is coupled to the right atrial lead 620, the coronary sinus lead 624, and the right ventricular lead 630 through the switch 674 to sample cardiac signals across any pair of desired electrodes. The microcontroller 660 is further coupled to a memory 694 by a suitable data/address bus 696, wherein the programmable operating parameters used by the microcontroller 660 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 694 through a telemetry circuit 700 in telemetric communication with the external device 702, such as a programmer, transtelephonic transceiver or a diagnostic system analyzer. The telemetry circuit 700 is activated by the microcontroller by a control signal 706. The telemetry circuit 700 advantageously allows intracardiac electrograms and status information relating to the operation of pacer/ICD 10 (as contained in the microcontroller 660 or memory 694) to be sent to the external device 702 through an established communication link 704. Pacer/ICD 10 further includes an accelerometer or other physiologic sensor 708, commonly referred to as a "rate-responsive" sensor because it is typically used to adjust pacing stimulation rate according to the exercise state of the patient. However, the physiological sensor 708 may, depending upon its capabilities, further be used to detect changes in cardiac output, changes in the physiological condition of the heart, or diurnal changes in activity (e.g., detecting sleep and wake states) and to detect arousal from sleep. Accordingly, the microcontroller 660 responds by adjusting the various pacing parameters (such as rate, AV Delay, V-V Delay, etc.) at which the atrial and ventricular pulse generators, 670 and 672, generate stimulation pulses. While shown as being included within pacer/ICD 10, it is to be understood that the sensor 708 may also be external to pacer/ICD 10, yet still be implanted within or carried by the patient. A common type of rate responsive sensor is an activity sensor incorporating an accelerometer or a piezoelectric crystal, which is mounted within the housing 640 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 710, which provides operating power to all of the circuits shown in FIG. 10. The battery 710 may vary depending on the capabilities of pacer/ICD 10. If the system only provides low voltage therapy, a lithium iodine or lithium copper fluoride cell may be utilized. For pacer/ICD 10, which employs shocking therapy, the battery 710 should be capable of operating at low current drains for long periods, and then be capable of providing high-current pulses (for capacitor charging) when the patient requires a shock pulse. The battery 710 should also have a predictable discharge characteristic so that elective replacement time can be detected. Accordingly, pacer/ICD 10 is preferably capable of high voltage therapy and batteries or other power sources appropriate for that purpose are employed.

As further shown in FIG. 10, pacer/ICD 10 is shown as having an impedance measuring circuit 712 which is enabled by the microcontroller 660 via a control signal 714. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 74 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 660 further controls a shocking circuit 716 by way of a control signal 718. The shocking circuit 716 generates shocking pulses of low (up to 0.5 joules), moderate (0.5-10 joules) or high energy (11 to 40 joules), as controlled by the microcontroller 660. Such shocking pulses are applied to the heart of the patient through at least two shocking electrodes, and as shown in this embodiment, selected from the left atrial coil electrode 628, the RV coil electrode 636, and/or the SVC coil electrode 638. The housing 640 may act as an active electrode in combination with the RV electrode 636, or as part of a split electrical vector using the SVC coil electrode 638 or the left atrial coil electrode 628 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 660 is capable of controlling the synchronous or asynchronous delivery of the shocking pulses.

Microcontroller 60 also includes an IEGM individual cardiac cycle integral-based respiration detector 701 for detecting respiration based upon IEGM signals using the techniques described above. An abnormal respiration pattern detector 703 is also provided the purposes of detecting apnea, hypopnea, etc. using techniques described above. Additionally, an abnormal respiration therapy controller 705 is provided for controlling therapy in response to an episode of abnormal respiration, again using techniques already described. Depending upon the implementation, the various components may be implemented as separate software modules. However, the modules may be combined so as to permit single modules to perform multiple functions.

What have been described are various systems and methods for tracking respiration, detecting episodes of abnormal respiration and delivering therapy in response thereto using an implantable system controlled by a pacer or ICD. However, principles of the invention may be exploiting using other implantable systems or in accordance with other techniques. Thus, while the invention has been described with reference to particular exemplary embodiments, modifications can be made thereto without departing from the spirit and scope of the invention.

What is claimed is:

1. A method for detecting respiration within a patient using an implantable medical device, the method comprising:
   delivering pacing pulses to the heart;
   sensing cardiac electrogram signals resulting from the pacing pulses using electrodes coupled to the heart;
   identifying individual complete cardiac cycles within the cardiac electrogram signals;
   determining values representative of integrals of cardiac electrogram signals corresponding to individual complete cardiac cycles; and
   detecting patient respiration based on the values representative of the integrals of the cardiac electrogram signals.

2. The method of claim 1 wherein delivering pacing pulses is performed to deliver atrial pacing pulses and wherein determining the values is performed to determine values representative of integrals of cardiac electrogram signals between consecutive atrial pacing pulses.

3. The method of claim 1 wherein delivering pacing pulses is performed to deliver ventricular pacing pulses and wherein determining values representative of integrals is performed to determine values representative of integrals of cardiac electrogram signals between consecutive ventricular pacing pulses.

4. The method of claim 1 wherein determining the values representative of integrals is performed by calculating a numerical sum of the absolute values of a plurality of individual voltage samples of the cardiac electrogram signal corresponding to a complete cardiac cycle.

5. The method of claim 1 further comprising detecting an episode of abnormal respiration based on patient respiration.

6. The method of claim 5 wherein the episode of abnormal breathing is one or more of apnea, hypopnea, hyperpnea, asthma, Cheyne-Stokes Respiration (CSR).

7. The method of claim 6 further comprising delivering therapy upon detection of an episode of abnormal respiration.

8. The method of claim 7 wherein the implantable device is equipped to deliver overdrive pacing therapy to the heart of the patient and wherein delivering therapy comprises delivering overdrive pacing therapy to the heart of the patient in response to an episode of apnea.

9. The method of claim 8 wherein the overdrive pacing therapy is dynamic atrial overdrive (DAO) pacing therapy.

10. The method of claim 7 wherein an implantable drug pump is provided and wherein delivering therapy comprises selectively delivering drug therapy to the patient using the drug pump.

11. The method of claim 10 wherein delivering therapy upon detection of an episode of abnormal respiration includes changing cardiac stimulation parameters.

12. The method of claim 11 wherein changing cardiac stimulation parameters is performed to increase a pacing rate.

13. The method of claim 5 further comprising generating a warning signal in response to an episode of abnormal respiration.

14. The method of claim 13 wherein generating a warning signal comprises one or more of: transmitting a signal to an external alarm device; electrically stimulating selected muscles of the patient to cause the muscles to twitch using an implantable electrical stimulator; or controlling an implantable device to vibrate.

15. The method of claim 1 further comprising recording diagnostic information representative of respiration.

16. A system for detecting respiration within a patient for use within an implantable medical device, the system comprising:
    pacing circuitry operative to deliver pacing pulses to the heart of the patient;
    sensing circuitry including electrodes coupled to the heart, operative to sense cardiac electrogram signals resulting from pacing pulses delivered by the pacing circuitry;
    a cardiac cycle integration unit operative to determine values representative of integrals of cardiac electrogram signals corresponding to individual complete cardiac cycles defined by consecutive pacing pulses; and
    a complete cardiac cycle integral-based respiration detector operative to detect patient respiration based on the values.

17. A system for detecting respiration within a patient for use within an implantable medical device, the system comprising:
    means coupled to the heart for delivering pacing pulses to the heart;
    means for sensing cardiac electrogram signals resulting from pacing pulses delivered to a heart;
    means for determining values representative of the area of the cardiac electrogram signals corresponding to individual complete cardiac cycles defined by consecutive pacing pulses; and
    means for detecting patient respiration based on the values.

18. The system of claim 17 and further comprising means for detecting an episode of abnormal respiration based on patient respiration.

19. The system of claim 18 wherein the episode of abnormal breathing is one or more of apnea, hypopnea, hyperpnea, asthma, Cheyne-Stokes Respiration (CSR).

20. The system of claim 18 further comprising means for delivering therapy upon detection of an episode of abnormal respiration.

* * * * *